US00PP36320P2

(12) United States Plant Patent
Moore et al.

(10) Patent No.: US PP36,320 P2
(45) Date of Patent: Dec. 17, 2024

(54) RASPBERRY PLANT NAMED 'WSU 2188'

(50) Latin Name: *Rubus idaeus L.*
Varietal Denomination: WSU 2188

(71) Applicant: Washington State University, Pullman, WA (US)

(72) Inventors: Patrick P. Moore, Pullman, WA (US); Wendy Hoashi-Erhardt, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

(21) Appl. No.: 18/445,560

(22) Filed: Oct. 17, 2023

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./156, 203, 204
See application file for complete search history.

*Primary Examiner* — Karen M Redden
(74) *Attorney, Agent, or Firm* — Barnes & Thornburg LLP

(57) ABSTRACT

This invention relates to a new and distinct variety of red raspberry plant (*Rubus idaeus L.*) named 'WSU 2188' from a controlled cross of two unnamed WSU raspberry selections that is different from its parents and other mid-season raspberries. 'WSU 2188' is primarily characterized by suitability for machine harvestability, adapted to the raspberry production area of the Pacific Northwest tolerance to root rot, mid-season production and large, conical fruit.

6 Drawing Sheets

STATEMENT REGARDING FEDERALLY-SPONSORED RESEARCH

This invention was made with government support under grant numbers 58-2072-9-027 and 58-5358-9-440 awarded by the United States Department of Agriculture through the Agricultural Research Service and grant number NI19HFPXXXXXG010 awarded by the United States Department of Agriculture through the National Institute of Food & Agriculture. The government has certain rights in the invention.

Latin name: This invention concerns a new and distinct cultivar of red raspberry plant with a botanical name of *Rubus idaeus L.*

Varietal denomination: The varietal denomination of the claimed raspberry is 'WSU 2188.'

FIELD OF THE INVENTION

This invention concerns a new and distinct cultivar of red raspberry plant with a botanical name of *Rubus idaeus L.* The intended market use for the fruit is as processed (frozen) or fresh.

BACKGROUND OF THE INVENTION

Raspberries are an economically important crop in the United States and many cultivars of raspberry plant are known. New cultivars of raspberry are needed to provide growers with resources for emerging disease, climate, and market conditions that affect production.

The present invention relates to a new and distinct floricane-bearing (summer fruiting on second year canes) red raspberry variety designated as 'WSU 2188'. The variety is botanically known as *Rubus idaeus L.* The new and distinct variety of red raspberry originated from a hand-pollinated cross of the 'WSU 1638' (unpatented) as the maternal parent and 'WSU 1447' (unpatented) as the paternal parent. 'WSU 1638' was selected from a cross made in 1999 and has good size and machine harvestability. 'WSU 1447' was selected from a cross made in 1996 and gives progeny that produce large, firm fruit suitable for machine harvesting.

The cross was made in Year 1 in Puyallup, WA. Seeds were germinated in the winter of Year 1-2 and the resulting seedlings planted in Year 2 with a cooperating raspberry grower in Burlington, WA. Selections were made in Year 4 using a raspberry machine harvester.

Varietal designation 'WSU 2188' was selected in Year 4 and asexually propagated in Puyallup, WA in tissue culture using meristem cultures from axillary buds of primocanes. This selection was planted in non-replicated plots with a cooperating grower in Year 5 and planted with a second grower in Year 8. The plantings were maintained by the growers using typical commercial growing practices and harvest methods. The plantings were subjectively evaluated weekly for adaptation to machine harvesting for two fruiting seasons. In all harvest seasons this selection machine harvested well and had large fruit size. This selection was tested for tolerance to root rot. Plants and fruit of this new variety have remained true to type through successive generations of asexual propagation. 'WSU 2188' is being named and released and is the subject of this invention.

SUMMARY OF THE INVENTION

The following traits have been repeatedly observed and are determined to be unique characteristics of 'WSU 2188', which in combination distinguish this raspberry plant as a new and distinct variety:

1. Large fruit size
2. Conic fruit shape, with fruit longer than broad
3. Tolerance to root rot 4. Suitability for machine harvesting
5. Long laterals and leaf stems that tend to droop 'WSU 2188' is distinguished from its maternal parent, 'WSU 1638', by larger fruit and firmer fruit.

'WSU 2188' is distinguished from its paternal parent, 'WSU1447', by larger fruit and softer fruit.

'WSU 2188' is distinguished from 'WSU 2166' (U.S. Plant Pat. No. 30,980), by later fruiting, firmer fruit, larger fruit, darker fruit and lower tolerance to root rot.

'WSU 2188' is distinguished from the most commonly grown red raspberry in the Pacific Northwest, 'Meeker' (unpatented), by larger fruit, firmer fruit, more drupelets per fruit, greater fruit length to width ratio and greater tolerance to root rot.

'WSU 2188' is distinguished from 'Willamette' (unpatented) by larger fruit, greater fruit length to width ratio, later fruiting, lighter colored fruit and greater tolerance to root rot.

BRIEF DESCRIPTION OF THE DRAWINGS

The accompanying photographs illustrate typical characteristics of the new variety 'WSU 2188' and are true to color as it is reasonably possible with color reproductions of this type. Color in the photographs may differ slightly from the color value cited in the detailed botanical description, which accurately describes the color of 'WSU 2188'. When objects could be accurately measured with an 8 mm diameter measuring opening (leaves, fruit and some canes), color was measured with a Minolta CR-400 Colorimeter, which measures color in L*, a*, b* color coordinates. Calibration was performed using a standard white plate supplied by the manufacturer. These L*, a*, b* coordinates were converted and are presented in Munsell color notation. For all other color measurements, color was compared with Munsell (1977) color plates.

DETAILED BOTANICAL DESCRIPTION

Figure 1:
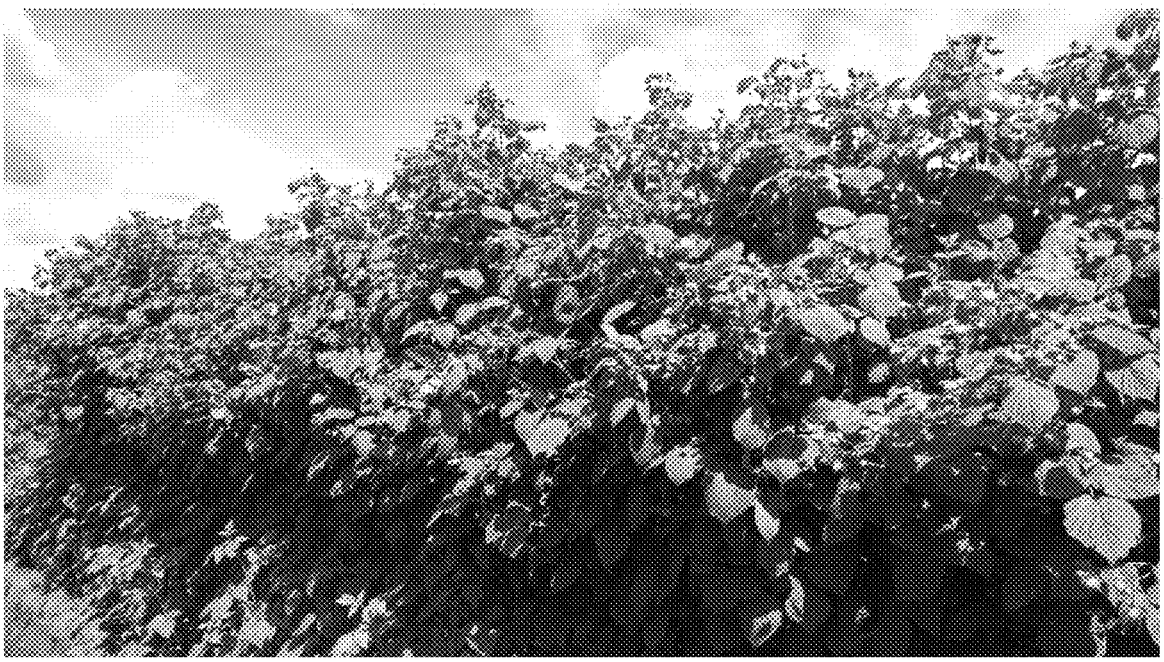
FIG. 1 is a picture of the growth habit of the plant and display of fruit on 16 June of Year 10, Lynden, WA.
Figure 2:
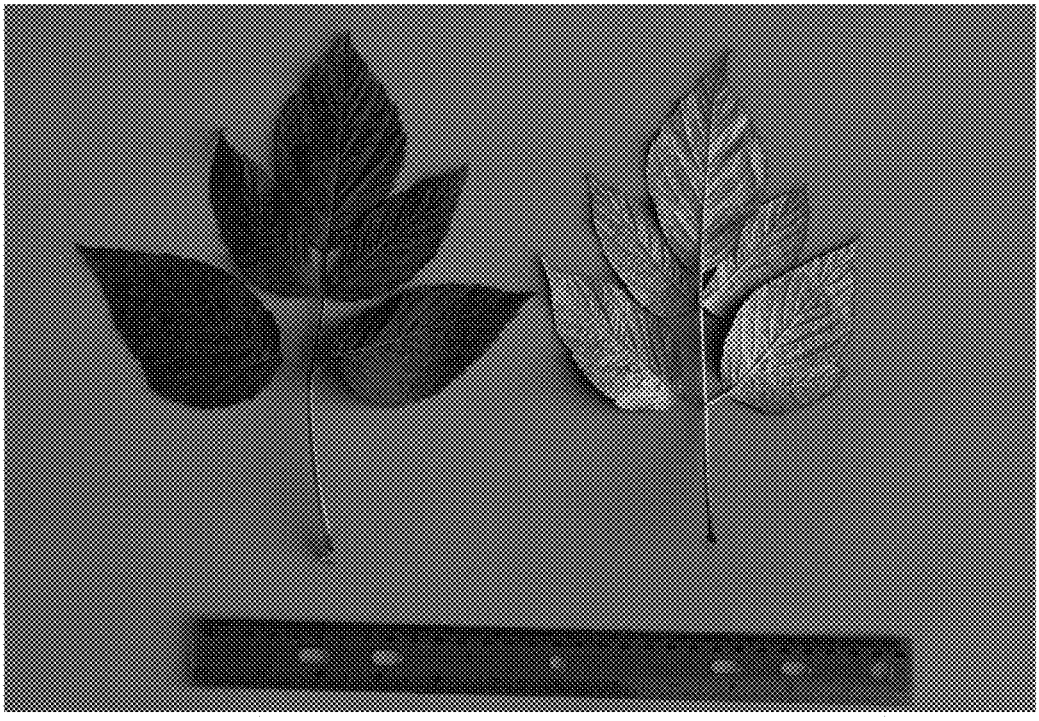
FIG. 2 is a photograph of the primocane leaves of 'WSU 2188' on 22 July of Year 17, Lynden, WA.
Figure 3:
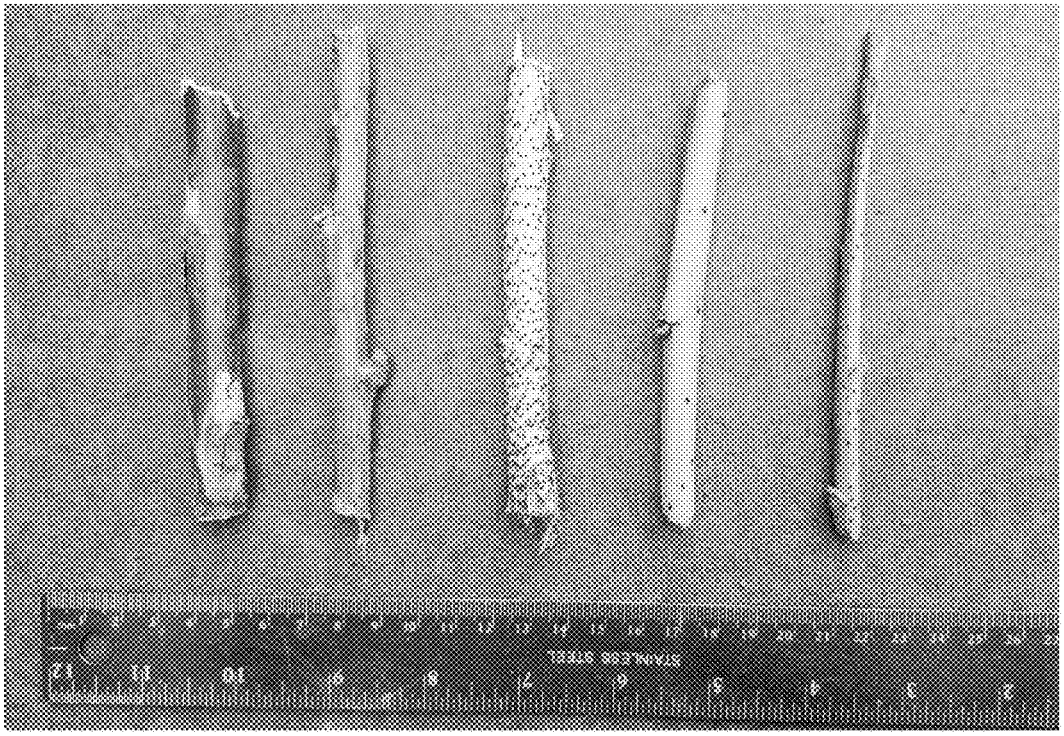
FIG. 3 is a photograph of cane segments of 'WSU 2188', from left to right: basal segment of floricane, mid-section of floricane, basal segment of primocane, mid-section of primocane, and upper section of primocane, taken 4 August of Year 17, Lynden, WA.
Figure 4:
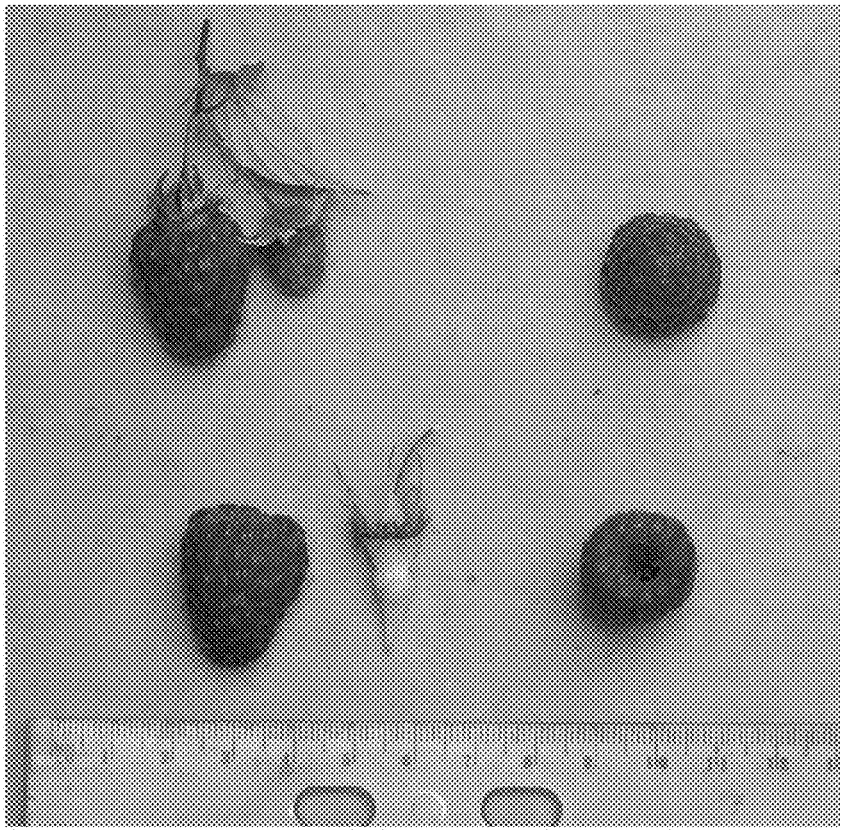
FIG. 4 is a photograph of fruit and receptacle of 'WSU 2188' taken July 16 of Year 13 in Lynden, WA.
Figure 5:
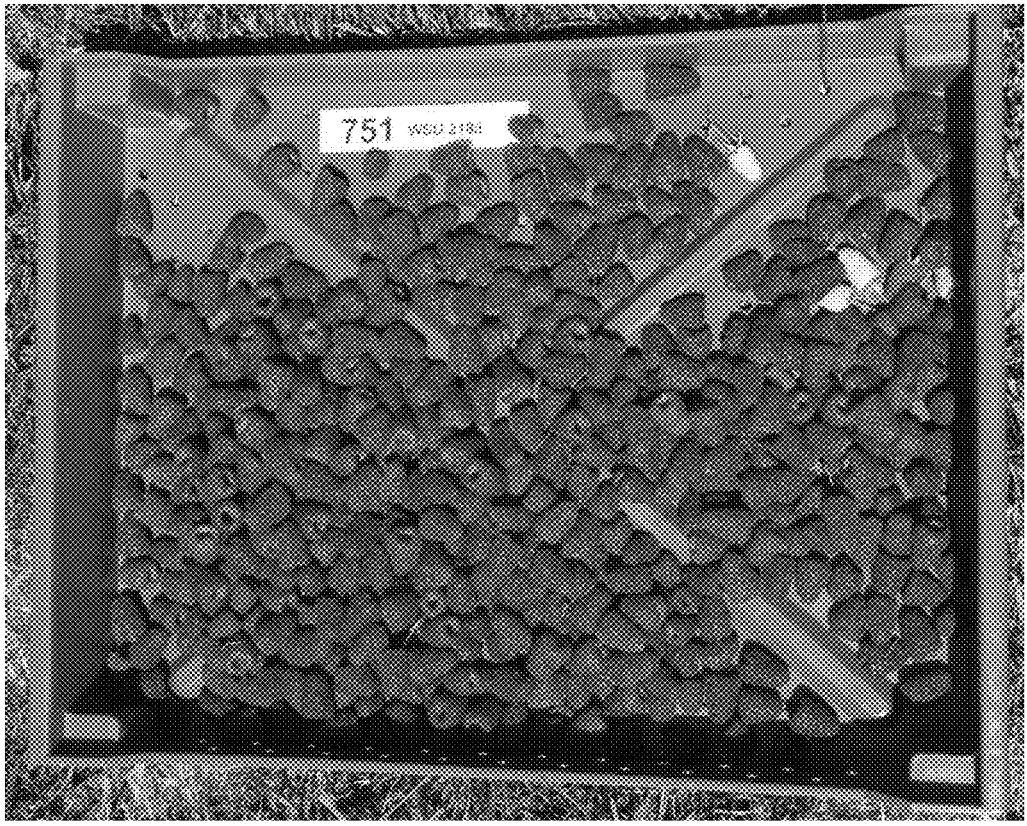
FIG. 5 is a photograph of machine harvested fruit of 'WSU 2188' taken 12 July of Year 10.
Figure 6:
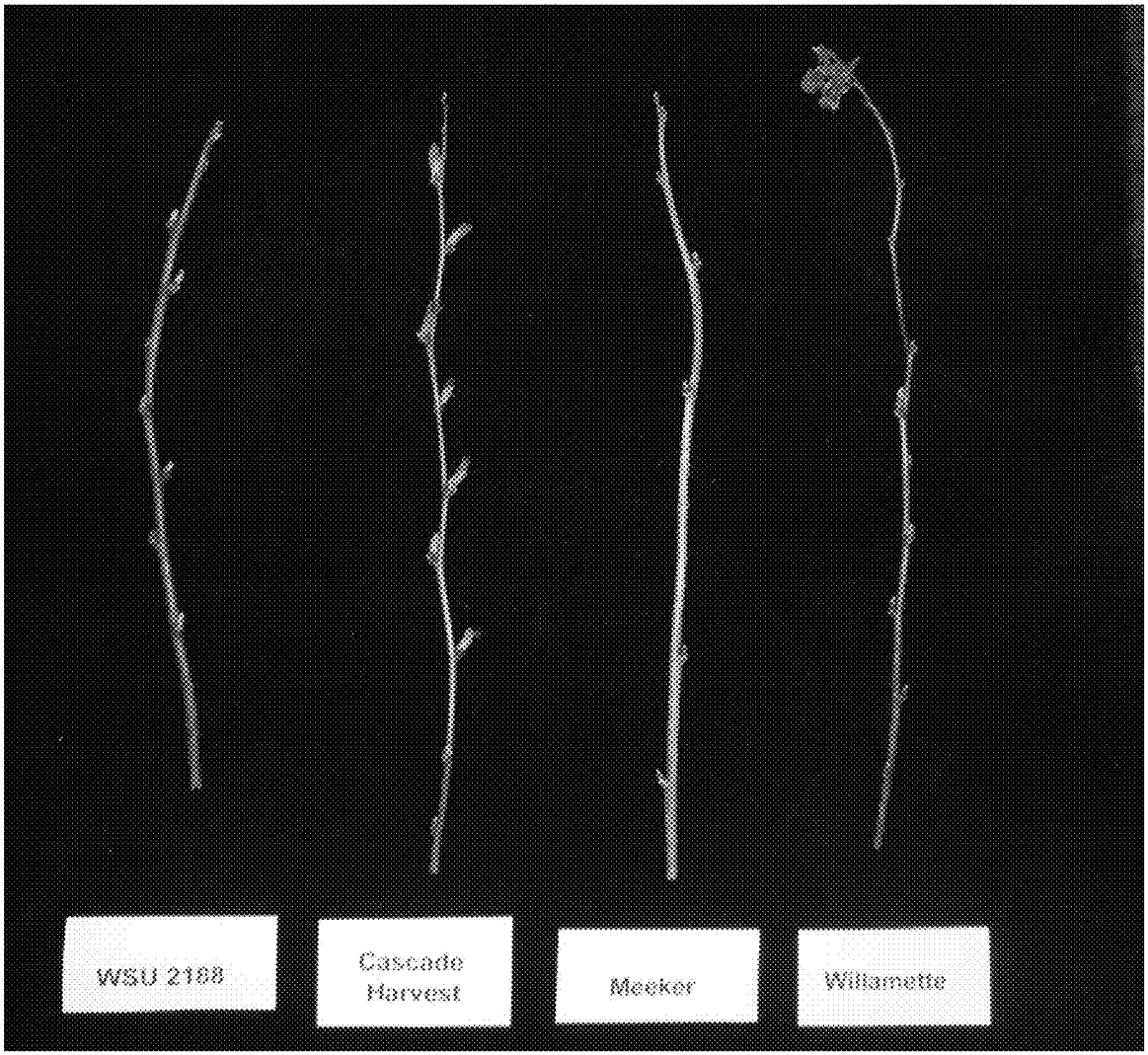
FIG. 6 is a photograph showing spring bud development of 'WSU 2188' relative to commonly grown cultivars taken 21 February Year 12, Puyallup, WA.

'WSU 2188' has not been observed under all possible environmental conditions and as such the characteristics may vary in detail depending on weather conditions, day length, soil type and location. The description is based on observations taken in Year 11 (except as noted) in Puyallup, WA and with cooperating growers in Lynden, WA.

A comparison of fruit of 'WSU 2188' with cultivars commonly grown in Washington is given in Table 1. 'WSU 2188' had greater machine harvest yield than 'Meeker' and 'Willamette' and lower yield than 'Cascade Harvest'. 'WSU 2188' had later midpoints of harvest than 'Willamette' and similar to 'Meeker'. In the Puyallup planting, 'WSU 2188' had lower yield in Year 10 than 'Cascade Harvest' but greater than 'Meeker' and 'Willamette'. In Year 11, yield of 'WSU 2188' was higher than all other cultivars. 'WSU 2188' had the largest fruit weight and firmest fruit of the genotypes tested. It had the lowest fruit rot in year 10 and second lowest in Year 11. 'WSU 2188' had midpoint of harvest a day earlier than 'Meeker' in Year 10 and four days later than 'Meeker' in Year 11.

TABLE 1

Harvest data.

| | 'WSU 2188' | 'Cascade Harvest' | 'Meeker' | 'Willamette' |
|---|---|---|---|---|
| Machine harvest, Lynden, WA[z] Yield (tons/acre) | | | | |
| Year 10 | 8.3 | 9.3 | 6.1 | 6.4 |
| Year 11 | 6.0 | 7.5 | 7.3 | 5.8 |
| Total | 14.3 | 16.8 | 13.4 | 12.2 |
| Midpoint of harvest | | | | |
| Year 10 | 7/2 | 7/1 | 7/3 | 6/22 |
| Year 11 | 7/19 | 7/17 | 7/19 | 7/12 |
| Hand harvest, Puyallup, WA[x] Yield (tons/acre) | | | | |
| Year 10 | 8.1 | 11.0 | 6.8 | 7.8 |
| Year 11 | 7.2 | 7.0 | 6.5 | 6.3 |
| Total Yield | 15.3 | 18.0 | 13.3 | 14.1 |
| Fruit weight (g) | | | | |
| Year 10 | 4.40 | 4.16 | 3.10 | 3.06 |
| Year 11 | 4.05 | 3.54 | 3.19 | 3.37 |
| Fruit firmness (g) | | | | |
| Year 10 | 102 | 90 | 74 | 74 |
| Year 11 | 168 | 107 | 107 | 122 |
| Fruit rot (%) | | | | |
| Year 10 | 7.8 | 9.8 | 11.4 | 7.2 |
| Year 11 | 5.7 | 14.5 | 10.6 | 6.6 |
| Midpoint of harvest | | | | |
| Year 10 | 6/27 | 6/23 | 6/28 | 6/19 |
| Year 11 | 7/13 | 7/11 | 7/9 | 7/5 |

[z]Harvest of non-replicated 8 plant plots.
[x]Harvest of 3 replications of 3 plants.

Table 2 provides information on the plant and fruit characteristics of the new variety 'WSU 2188' compared with 'Cascade Harvest' and 'Meeker', varieties grown commercially in Washington.

TABLE 2

Measurements of plant characteristics of 'WSU 2188' with two commercial varieties.

| | 'WSU 2188' | 'Cascade Harvest' | 'Meeker' |
|---|---|---|---|
| Plant height (m) | 1.91 | 1.91 | 1.91 |
| Plant width (m) | 1.40 | 1.09 | 1.35 |
| Self-fertile | yes | yes | yes |

TABLE 2-continued

Measurements of plant characteristics of 'WSU 2188' with two commercial varieties.

| | 'WSU 2188' | 'Cascade Harvest' | 'Meeker' |
|---|---|---|---|
| Flower measurements[x] | | | |
| Date of first bloom | 5/13 | 5/9 | 5/10 |
| Length of bloom (days) | 31 | 28 | 31 |
| Number of petals | 5 | 5 | 5 |
| Length of petal (mm) | 7.07 | 6.09 | 6.01 |
| Width of petal (mm) | 3.74 | 3.50 | 4.13 |
| Color petal upper surface (Munsell) | N9.5 | N9.5 | N9.5 |
| Color petal lower surface (Munsell) | N9.5 | N9.5 | N9.5 |
| Petal shape | Oblanceolate | Oblanceolate | Oblanceolate |
| Petal margin | Entire | Entire | Entire |
| Petal Texture | smooth | smooth | smooth |
| Flower diameter petal tip to petal tip at widest part of the flower (mm) | 20.2 | 17.9 | 17.8 |
| Number of sepals | 5 | 5 | 5 |
| Color sepal upper surface (Munsell) | 5GY 5/4 | 5GY 7/6 | 7.5GY 7/6 |
| Color sepal lower surface (Munsell) | 5GY 5/4 | 5GY 7/8 | 5GY 7/6 |
| Length of sepal (mm) | 8.70 | 6.93 | 7.56 |
| Width of sepal (mm) | 6.25 | 5.55 | 5.40 |
| Flower diameter sepal tip to sepal tip at the widest part of the flower (mm) | 27.5 | 21.0 | 20.8 |
| Number of stigma/flower | 67 | 73 | 61 |
| Number of anthers/flower | 63 | 92 | 65 |
| Flower fragrance | none noted | none noted | none noted |
| Pollen color | N 9.5 | N 9.5 | N 9.5 |
| Fruit Measurements | | | |
| Fruit color (Munsell) | 5.3R 2.6/5.7 | 5.8R 2.5/4.9 | 5.1R 2.6/5.1 |
| Fruit weight (g) | 5.3 | 5.7 | 3.8 |
| Fruit length (mm) | 28.5 | 28.4 | 21.7 |
| Fruit width (mm) | 20.6 | 22.3 | 20.0 |
| Fruit length/width ratio | 1.39 | 1.27 | 1.09 |
| Pedicel length (mm) | 29.8 | 27.8 | 16.2 |
| Pedicel width (mm) | 1.0 | 1.0 | 1.0 |
| Receptacle length (mm) | 23.2 | 22.0 | 16.8 |
| Receptacle width (mm) | 8.1 | 8.9 | 9.0 |
| Drupelet length (mm) | 5.6 | 5.2 | 5.1 |
| Drupelet width (mm) | 4.1 | 4.5 | 3.7 |
| Drupelet weight (mg) | 49.7 | 51.1 | 33.1 |
| Number of seeds per fruit | 107 | 112 | 114 |
| Seed weight (mg) | 2.02 | 1.95 | 1.70 |
| Primocanes | | | |
| Number of primocanes/hill | 16 | 26 | 18 |
| Length of primocane (m) | 2.12 | 2.19 | 2.55 |
| Diameter at ground (mm) | 9.5 | 11.5 | 11.9 |
| Diameter at 1.2 m (mm) | 7.9 | 9.8 | 8.8 |
| Number of nodes | 35 | 43 | 50 |
| Internode length at 1.2 m (cm) | 7.8 | 11.2 | 7.5 |
| Color primocane spines (Munsell) | 2.5R 4/2 | 2.5R 4/2 | 2.5R 4/2 |
| Length spine (mm) | 1.9 | 2.3 | 1.5 |
| Length base of spine (mm) | 2.6 | 2.9 | 1.4 |
| Width base of spine (mm) | 1.1 | 1.4 | 0.9 |
| Color spine base (Munsell) | 2.5R 4/2 | 2.5R 4/2 | 5R 5/10 |
| Primary cane color (Munsell) | 2.5GY 7/6 | 1.3GY 6.5/3.9 | 2.2GY 6.6/4.0 |
| Secondary cane color (Munsell) | 6YR 6/5 | 6.6R 3.8/4.8 | 7.9R 3.9/4.5 |

TABLE 2-continued

Measurements of plant characteristics of 'WSU 2188' with two commercial varieties.

| | 'WSU 2188' | 'Cascade Harvest' | 'Meeker' |
|---|---|---|---|
| Primocane fruiting | no | no | no |
| Pubescence on canes | absent | absent | slight |
| Color primocane leaves (Munsell)[y] | | | |
| Terminal Leaflet | | | |
| Upper surface | 5.7GY 3.7/4.7 | 6.1GY 3.5/3.8 | n.d. |
| Lower surface | 4.6GY 6.0/1.5 | 5.0GY 5.5/1.7 | n.d. |
| Distal Lateral Leaflets | | | |
| Upper surface | 5.5GY 4.0/4.2 | 6.2GY 3.4/3.7 | n.d. |
| Lower surface | 4.6GY 6.0/1.4 | 5.1GY 5.5/1.9 | n.d. |
| Basal Leaflets | | | |
| Upper surface | 6.0GY 3.6/3.6 | 6.2GY 3.3/3.8 | n.d. |
| Lower surface | 4.7GY 6.0/1.6 | 5.9GY 5.4/1.9 | n.d. |
| Primocane leaves | | | |
| Number of leaflets | 5 | 5 | 5 |
| Petiole length (mm) | 93 | 99 | 89 |
| Rachis length (mm) | 39 | 51 | 41 |
| Stipule (mm) | 6.7 | 8.3 | 11.3 |
| Leaflet margins | doubly serrated | doubly serrated | doubly serrated |
| Leaflet overlap | occasionally overlap | occasionally overlap | commonly overlap |
| Terminal leaflet | | | |
| Length (mm) | 116 | 104 | 103 |
| Width (mm) | 56 | 67 | 68 |
| Length/width | 2.1 | 1.5 | 1.5 |
| Leaflet tip | cuspidate | cuspidate | cuspidate |
| Leaflet base | oblique | cordate | obtuse |
| Distal lateral leaflet | | | |
| Length (mm) | 80 | 83 | 78 |
| Width (mm) | 31 | 41 | 39 |
| Length/width | 2.6 | 1.6 | 1.6 |
| Petiolule length (mm) | 0 | 1.6 | 1.6 |
| Leaflet tip | cuspidate | cuspidate | cuspidate |
| Leaflet base | obtuse | oblique | oblique |
| Basal leaflet | | | |
| Length (mm) | 96 | 95 | 98 |
| Width (mm) | 52 | 58 | 60 |
| Length/width | 1.8 | 1.6 | 1.6 |
| Petiolule length (mm) | 9.9 | 3.4 | 3.8 |
| Leaflet tip | cuspidate | cuspidate | cuspidate |
| Leaflet base | obtuse | oblique | oblique |
| Floricanes | | | |
| Primary cane color (Munsell) | 2.3Y 5.5/5.5 | 1.3GY 6.5/3.9 | 2.2GY 6.6/4.0 |
| Secondary cane color (Munsell) | 5.1YR 4.1/3.5 | 6.6R 3.8/4.8 | 7.9R 3.9/4.5 |
| Primocane fruiting | no | no | no |
| Pubescence on canes | absent | absent | slight |
| Number of floricanes/hill | 10.0 | 10.0 | 10.0 |
| Diameter at base (mm) | 10.5 | 9.8 | 11.4 |
| Diameter at 1.2 m (mm) | 7.9 | 7.6 | 11.1 |
| Internode length at 1.2 m (cm) | 5.1 | 6.6 | 6.9 |
| Height (m) | 1.7 | 1.7 | 1.7 |
| Lateral length 1.2 m (cm) | 145 | 146 | 140 |

TABLE 2-continued

Measurements of plant characteristics of 'WSU 2188' with two commercial varieties.

| | 'WSU 2188' | 'Cascade Harvest' | 'Meeker' |
|---|---|---|---|
| Nodes/lateral | 12.2 | 11.3 | 12.7 |
| Number fruit/lateral | 19.0 | 21.0 | 15.0 |
| Number fruit/fruiting node | 3.5 | 3.7 | 2.1 |
| Color floricane leaves[z] | | | |
| Terminal Leaflet | | | |
| Upper surface | 5.9GY 3.4/3.8 | 5.4GY 3.5/3.4 | n.d. |
| Lower surface | 4.4GY 6.0/1.4 | 5.5GY 5.5/1.8 | n.d. |
| Basal Leaflet | | | |
| Upper surface | 3.9GY 4.1/4.5 | 6.4GY 3.3/3.7 | n.d. |
| Lower surface | 4.7GY 5.7/1.6 | 5.6GY 5.6/1.8 | n.d. |
| Floricane leaves | | | |
| Leaflet number | 3 | 3 | 3 |
| Petiole length (mm) | 42 | 47 | 53 |
| Leaflet margins | doubly serrated | doubly serrated | doubly serrated |
| Terminal leaflet | | | |
| Length (mm) | 99 | 87 | 93 |
| Width (mm) | 67 | 80 | 61 |
| Length/width | 1.5 | 1.1 | 1.5 |
| Petiolule (mm) | 28.0 | 30.2 | 24.5 |
| Basal leaflet | | | |
| Length (mm) | 84 | 78 | 76 |
| Width (mm) | 46 | 48 | 43 |
| Length/width | 1.8 | 1.6 | 1.8 |
| Petiolule (mm) | 9.6 | 2.8 | 2.0 |

[x]Flower measurements made in Year 13.
[y]Average color measurements for two leaflets of distal lateral and basal leaflets.
[z]Average color measurements for two leaflets of basal leaflets.

Machine harvested fruit was collected in Lynden, WA and analyzed in Years 7, 8 and 10. 'WSU 2188' had slightly lower soluble solids than 'Meeker' and higher titratable acidity and lower pH than 'Meeker' and 'Willamette', resulting in a slightly more tart flavor. Table 3 provides the comparative values for anthocyanin content, soluble solids, pH and titratable acidity of raspberry fruit for the 'WSU 2188', 'Meeker' and 'Willamette' varietals.

TABLE 3

Anthocyanin content, soluble solids, pH and titratable acidity of raspberry fruit machine average of fruit harvested in years 2013, 2014 and 2017 at Lynden, WA. Based on fruit samples of approximately 300 g collected for each cultivar.

| | WSU 2188 | Cascade Premier | Meeker | Willamette |
|---|---|---|---|---|
| Soluble solids (deg. Brix) | 9.1 | 7.5 | 9.4 | 8.4 |
| pH | 3.10 | 3.25 | 3.45 | 3.26 |

TABLE 3-continued

Anthocyanin content, soluble solids, pH and titratable acidity of raspberry fruit machine average of fruit harvested in years 2013, 2014 and 2017 at Lynden, WA. Based on fruit samples of approximately 300 g collected for each cultivar.

| | WSU 2188 | Cascade Premier | Meeker | Willamette |
|---|---|---|---|---|
| Titratable acidity[z] (% citric acid) | 1.96 | 1.72 | 1.88 | 1.52 |
| Total anthocyanins[y] (mg C-3-G/100 g FW) | 82 | 46 | 57 | 95 |

[z]Acidity expressed as % citric acid.
[y]Total anthocyanins determined spectrophotometrically from acidified ethanol extracts and expressed as cyanidin-3-glucoside.

Table 4 provides the root rot evaluation of 'WSU 2188', 'Cascade Harvest' and 'Meeker,' which were evaluated for susceptibility to root rot in plots at the Goss Farm, Puyallup, WA in plantings established in Year 8. The presence of *Phytophthora fragariae var rubi* ([W.F. Wilcox & J.M. Duncan] W.A. Man in't Veld,) in these root rot plots has been verified via PCR. Four plants of each clone were planted in this area. Plants were subjectively rated for vigor in the fall of each year from 0 to 5, with 0 being dead and 5 a healthy and vigorous plant. Year 11 was a very severe root rot test. Other raspberries in the same planting had a decrease in their vigor ratings by an average of over 40% from Year 10 to Year 11. In the fall of the fourth year, 'WSU 2188' plants had a rating of 3.5, while 'Meeker' averaged 2.5 and 'Cascade Harvest' averaged 1.0. Based on this trial, 'WSU 2188' demonstrates a relatively high root rot tolerance, although it is not absolutely unaffected.

TABLE 4

Root rot evaluation[x]

| Date | 'WSU 2188' | 'Cascade Cascade Harvest' | 'Meeker' |
|---|---|---|---|
| Nov. 6, 2015 | 4.00 | 4.25 | 4.00 |
| Nov. 4, 2016 | 3.33 | 5.00 | 4.75 |
| Sep. 13, 2017 | 3.00 | 1.00 | 2.50 |

[x]Four plants of each cultivar planted in Year 8. Subjectively rated 0-5. 0 = dead, 5 = healthy and vigorous.

'WSU 2188' was planted in non-replicated plots with cooperating growers in Year 5 and Year 8. The plantings were maintained by growers using typical commercial methods and the fruit machine harvested. The plantings were subjectively evaluated for adaptation to machine harvesting weekly during the harvest season for two fruiting seasons. In all harvest seasons 'WSU 2188' machine harvested well and was productive with large fruit size. Based on these evaluations, 'WSU 2188' is suitable for machine harvesting. At most locations where 'WSU 2188' has been tested, no winter injury has been observed. In one location near Lynden, Washington, 'WSU 2188' showed a minimal amount of winter injury in one season. Drought and heat tolerance response are not known.

Table 5 provides fruit weight, firmness, and color measurements before and after storage for fruit of 'WSU 2188' and comparison cultivar Cascade Harvest. At harvest time the average fruit weight of WSU 2188 was 4.20 g before storage and 2.81 g after 14 days of storage. The average weight of 'Cascade Harvest' was 4.04 g before storage and 2.50 g after storage. The average firmness of 'WSU 2188' fruit before storage was 223.5 g and after storage was 68.5 g. The average firmness of 'Cascade Harvest' fruit before storage was 90.2 g and after storage was 27.0 g. 'WSU 2188' had larger, firmer and a darker red color (data not shown) than 'Cascade Harvest' both before storage and after storage.

TABLE 5

Fruit weight and firmness before and after storage for hand-harvested fruit of two cultivars in plots Puyallup, WA.

| | Fruit weight (g) | | Firmness (g) | |
|---|---|---|---|---|
| Clone | Before storage[z] | After storage | Before storage | After storage |
| 'WSU 2188' | 4.20 | 2.81 | 223.5 | 68.5 |
| 'Cascade Harvest' | 4.04 | 2.50 | 90.2 | 27.0 |

[z]Values represent means of 10 fruit per cultivar. Fruit were harvested 3 Jul. 2017, with data collected on individual fruit. Firmness was destructively measured on 10 fruit of each cultivar that were subsequently discarded. Fruits were stored at 4° C. for seven d, then brought to room temperature (~20° C.) for 4 h for after storage measurements.

The invention claimed is:

1. A new and distinct variety of raspberry plant, designated 'WSU2188', substantially as illustrated and described herein.

* * * * *